United States Patent [19]

Polski et al.

[11] Patent Number: 5,599,601
[45] Date of Patent: Feb. 4, 1997

[54] DIAPER FASTENING TAPE

[75] Inventors: Stephen P. Polski, Shoreview; Jayshree Seth, Woodbury; Charles E. Boyer, III, Oakdale, all of Minn.

[73] Assignee: Minnesota Mining and Manufacturing Company, St. Paul, Minn.

[21] Appl. No.: 370,967

[22] Filed: Jan. 10, 1995

Related U.S. Application Data

[62] Division of Ser. No. 277,620, Jul. 20, 1994, abandoned.

[51] Int. Cl.$^6$ ......................................... B32B 3/06
[52] U.S. Cl. .................. 428/40.1; 428/41.7; 428/41.8; 428/41.9; 428/99; 428/121; 428/214; 428/352; 428/354; 428/355 RA; 428/355 AC; 604/389; 604/390
[58] Field of Search .............................. 428/40, 355, 354, 428/402, 40.1, 41.7, 41.8, 41.9, 99, 352, 121, 214; 604/389, 390

[56] References Cited

U.S. PATENT DOCUMENTS

| | | | |
|---|---|---|---|
| 3,955,576 | 5/1976 | Safford | 128/287 |
| 3,983,166 | 9/1976 | Samour | 260/481 R |
| 4,029,098 | 6/1977 | Karami | 128/284 |
| 4,060,085 | 11/1977 | Karami | 128/287 |
| 4,168,196 | 9/1979 | Nemeth et al. | 156/184 |
| 4,237,890 | 12/1980 | Laplanche | 128/287 |
| 4,379,201 | 4/1983 | Heilmann et al. | 428/345 |
| 4,585,450 | 4/1986 | Rosch | 604/390 |
| 4,726,971 | 2/1988 | Pape et al. | 428/40 |
| 5,342,685 | 8/1994 | Gobran | 428/355 |

FOREIGN PATENT DOCUMENTS

| | | |
|---|---|---|
| 0375862 | 7/1990 | European Pat. Off. . |
| 0563458 | 10/1993 | European Pat. Off. . |
| 2267058 | 11/1975 | France . |
| WO89/12618 | 12/1989 | WIPO . |

*Primary Examiner*—Nasser Ahmad
*Attorney, Agent, or Firm*—Gary L. Griswold; Walter N. Kim; William J. Bond

[57] ABSTRACT

A disposable tape tab for a diaper or a like article is provided with at least a fastening tape tab portion and a release tape tab portion, the fastening tape tab portion having a fastening surface which fastening surface is on a face opposite the adhesive surface face of the release tape tab portion. The fastening tape tab portion and said release tape tab portion are joined by at least one adhesive-to-substrate bond with no adhesive layer to adhesive layer contact. Preferably the fastening surface on the fastening tape tab is a pressure sensitive adhesive, with both the fastening tape tab and the release tape tab having a release layer on the face opposite the face having the adhesive layer.

12 Claims, 3 Drawing Sheets

DIAPER FASTENING TAPE

This is a division of application Ser. No. 08/277,620 filed Jul. 20, 1994, now abandoned.

The present invention relates to an adhesive closure fastening tape and release tape structure for use in a disposable diaper or an adult incontinent article. The fastening tape and release tapes are designed to be supplied as separate tape elements, which can be assembled by a diaper manufacturer on the diaper line.

Many of the original disposable diapers used pressure-sensitive adhesive fastening tape tabs. The adhesive on the free end, or outer end of the fastening tape tab required protection from contamination prior to use. This protection was provided with a disposable release liner. However these early disposable release liner were considered to be undesirable for a number of reasons including; inconvenience, difficulty of use, and fear of a baby inadvertently swallowing the detachable disposable release liner. In response to these problems a number of patent applications were filed directed at various means of eliminating or modifying the disposable release liner. Some of these patents are discussed in U.S. Pat. No. 4,168,196.

U.S. Pat. No. 4,168,196 is directed to an alternative method of eliminating the disposable release liner so as to minimize the amount of substrate film used in forming the diaper fastening tape tab. A single substrate film is zone coated with adhesive and release material on opposing faces and ends of the substrate. There are two adhesive regions on different faces, and opposing ends, of the substrate with two release coated regions provided opposite the adhesive regions so that the substrate can be wound as a tape with the two adhesive regions in contact with the two release coatings. The fastening tape is adhered to the non-woven topsheet of the diaper with one adhesive region. The second adhesive region on the opposing end of the fastening tab is attached to the diaper backsheet by the user. This system while relatively simple to use by the diaper manufacturer is extremely difficult to manufacture requiring complicated zone coating of two distinct release coatings and two adhesive layers on a single substrate backing.

A more typical approach was the use of a separate fastening tape tab and release tape tab or release liner where the release tape or release liner is permanently secured to the diaper, the fastening tape tab or both. For example, U.S. Pat. No. 3,955,576 proposes attaching a fastening tape to a release tape, which release tape is also permanently attached to the diaper topsheet, bonding between the fastening tape to the release tape is created by overlapping the tapes to form an adhesive-to-adhesive contact region between the two tapes. U.S. Pat. No. 4,237,890 provides a release liner which is permanently attached at one face to a central section or zone of a fastening tab. One end section of the fastening tab is releasably attached to the release liner and the opposing end section of the fastening tab is permanently attached to the diaper backsheet. The tape laminate would apparently be supplied as a folded prelaminate structure. Another folded prelaminate structure is disclosed in U.S. Pat. No. 4,726,971 where a release tape is secured to a fastening tape by a unifying strip. The fastening tape and the release tape are permanently attached to opposing faces of the diaper. The fastening tape tab fastening end section is releasably secured to the release surface of the release tape. The fastening tape tab end permanently adhered to the diaper is provided with a distinct more aggressive adhesive layer. U.S. Pat. Nos. 4,060,085 and 4,029,098 propose a release liner which is adhesively secured to a central portion of the fastening tape tab at one end with most of the release liner heat sealed to the inner topsheet face of the diaper. These constructions are much more difficult for a diaper manufacturer to implement and the heat sealing of the release liner to the diaper can effectively destroy the release, characteristics of the release surface.

The present invention is directed at providing a low cost pressure-sensitive adhesive fastening tape and release tape system which is both simple to manufacture by the tape manufacturer and simple and economical for the diaper use in manufacturing a diaper tape closure system.

SUMMARY OF THE INVENTION

According to the present invention a disposable diaper or adult incontinent article is provided with a pressure-sensitive adhesive tape closure system comprising a closure tape laminate of a fastening tape tab portion and a release tape tab portion. Each tape tab portion has a first face with an adhesive layer and a second opposing face with no adhesive layer. The second faces preferable have a release layer allowing the fastening tape, the release tape and/or the closure tape laminate to be wound into a tape roll and subsequently unwound.

When the closure tape laminate is formed, with the two tapes flat and in the same plane, the two tape tab portions first faces are in face-to-face relation and partially overlapping. The two tape tab portions are connected to each other by a small portion of either the fastening tape tab portion adhesive layer or the release tape tab portion adhesive layer, or both, such that there is no adhesive contact between the two adhesive layers.

When in use the closure tape laminate release tape tab portion is adhered to the diaper topsheet (the liquid permeable inner layer) with the release tape tab portion adhesive layer. The fastening tape tab portion adhesive layer is releasably secured to a release surface on the second face of the release tape tab portion such that the fastening tape tab portion may be removably fastened to the second face of the release tape tab portion and subsequently adhered to the diaper backsheet to form the diaper closure.

DETAILED DESCRIPTION OF PREFERRED EMBODIMENTS

The pressure-sensitive adhesive tape tab closure system of the present invention will generally be described with reference to disposable diapers and adult incontinent articles, however, the invention closure tape laminates would be applicable to other disposable garments or closure systems for example in packaging, such as for an individual sanitary napkin wrapper.

Figure 1:
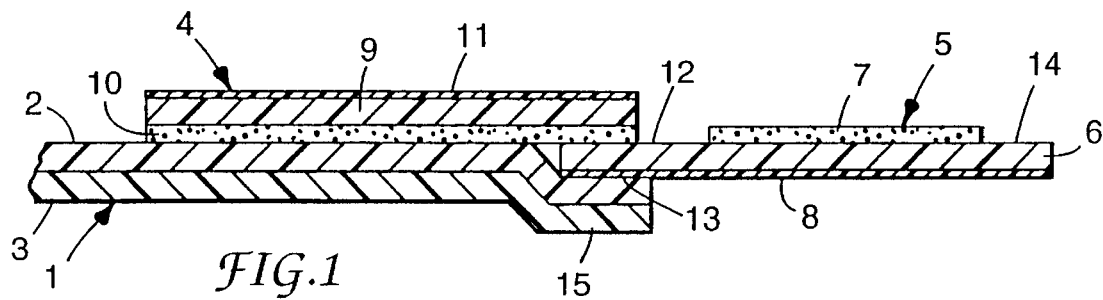
FIG. 1 is a side cross-sectional view of a first embodiment of the invention closure tape laminate on a diaper side edge.

FIG. 1 discloses a first embodiment of the present invention where the closure tape laminate comprises a release tape tab portion 4 and a fastening tape tab portion 5. The closure tape laminate is attached to a edge portion of a diaper chassis 1 comprising liquid permeable top sheet layer 2 and a liquid impermeable backsheet layer 3 which two layers (2 and 3) comprise the outer edge region of the diaper chassis 1. This outer edge region is where a closure tape is conventionally attached. The two tape tab portions (4 and 5) are attached to each other at an adhesive layer (7 or 10)-to-substrate bond area 13.

The release tape tab portion 4 comprises a substrate 9 provided with a release surface 11 on a second face with a first face coated with a pressure-sensitive adhesive layer 10. Substrate 9 can be any conventional film, such as a single or multi-layer film of thermoplastic polymer or polymers, such as polyolefins. Also non-woven or woven webs can be extrusion coated or laminated to additional layers, paper, films or the like to form substrate 9. The release surface 11 would typically be a release coating, which would be any type conventionally used as a release coating on a diaper release tape or release liner.

Pressure-sensitive adhesive layer 10 is formulated with an adhesive which will permanently bond the release tape tab portion 4 to the diaper topsheet 2 and would conventionally be a tackified rubber or synthetic rubber-resin type adhesive. A preferred adhesive would comprise that disclosed in U.S. Pat. No. 5,342,685 (Gobran), which discloses an adhesive comprising 100 parts of an elastomeric phase having 78–98 parts of an elastomeric diblock A-B type block copolymer of predominately polystyrene, or polystyrene derivative, A blocks and poly-1,3-butadiene B blocks. The remaining portion of the elastomeric phase multiblock A-B type block copolymers of three or more blocks is preferably an ABA triblock copolymer with the B block a poly-1,3-butadiene. The elastomeric phase is tackified with an admixture of a solid tackifying resin and an oil or liquid tackifier, at least partially compatible with the B blocks, to provide an adhesive having a composite midblock glass transition temperature (CMTg) of less than −10° C. Other tackified synthetic rubber or natural rubber pressure-sensitive adhesives can be used provided that the initial 135° peel (tested as described in U.S. Pat. No. 5,342,685 to the diaper topsheet (e.g. a nonwoven) is at least 100 gm/in, preferably at least 150 gm/in.

Fastening tape tab portion 5 similarly is comprised of a substrate 6, which can be any suitable substrate, such as those described for the release tape tab portion substrate 9. The fastening tape tab adhesive layer 7 can be any conventional pressure-sensitive adhesive used on a diaper fastening tape. In a preferred embodiment a less aggressive adhesive is used as the fastening tape adhesive with at least one adhesive-free region provided on the first adhesive coated face of substrate 6. This adhesive free region is used to form the substrate-to-adhesive layer bond 13 between the release tape tab portion pressure-sensitive adhesive layer 10 and the fastening tape tab portion substrate 6. Optionally a second pressure-sensitive adhesive free region can be provided at the opposite end of the fastening tape tab portion 5 to provide a tack free fingerlift portion for removing the fastening tape tab portion 5 from the release tape tab portion 4 release surface 11, or a suitable attachment region on the diaper chassis 1, or the like. Generally the fastening tape tab portion 5 is further provided with a release layer 8 allowing the fastening tape tab portion, or the closure tape laminate including the fastening tape tab portion 5, to be formed from a tape roll of the pressure-sensitive adhesive coated substrate(s) (9 and/or 6).

Less aggressive adhesives are required for the fastening tape tab portion (5) when the fastening tape tab portion (5) adheres directly to a thin film, or the like, backsheet layer to form the diaper closure. This, e.g., thin film is generally a polyethylene polymer, copolymer or blend film.

A low tack adhesive for releasably adhering to a thin film is based on free radically polymerizable acrylate pressure-sensitive adhesives preferably prepared by an emulsion polymerization process. These acrylates are typically alkyl acrylates, preferably monofunctional unsaturated acrylate esters of non-tertiary alkyl alcohols, the alkyl groups of which have from 2 to about 14 carbon atoms providing a polymer having a Tg of less than 0° C., preferably less than −10° C. Included with this class of monomers are, for example, isooctyl acrylate, isononyl acrylate, 2-ethylhexyl acrylate, decyl acrylate, dodecyl acrylate, n-butyl acrylate, and hexyl acrylate. The alkyl acrylate monomers can be used to form homopolymers or they can be copolymerized with polar copolymerizable monomers or high Tg monomers (higher than the alkyl acrylate) such as vinyl esters, $C_1$ to $C_{14}$ alkyl esters of (meth)acrylic acid and/or styrene. When copolymerized with moderately polar monomers, the alkyl acrylate monomer generally comprises at least about 70% of the polymerizable monomer composition. High Tg monomers can be used in amounts up to 20% of the monomer composition, preferably from 3 to 15 percent, most preferably 6 to 10 percent.

The polar copolymerizable monomers can be selected from strongly polar monomers such as monoolefinic mono- and dicarboxylic acids, hydroxyalkyl acrylates, cyanoalkyl acrylates, acrylamides or substituted acrylamides, or from moderately polar monomers such as N-vinyl pyrrolidone, acrylonitrile, vinyl chloride or diallyl phthalate. The strongly polar monomer preferably comprises up to about 25%, more preferably up to about 15%, of the polymerizable monomer composition. The moderately polar monomer preferably comprises up to about 30%, more preferably from about 2% to about 20% of the polymerizable monomer composition.

Optionally a low molecular weight hydrophobic polymer can be added to the adhesive matrix monomers to improve emulsion stability. These polymers would have an average molecular weight of from 400 to 50,000 and include polystyrene resins, poly(methylmethacrylate) resin, polybutadiene, polyisoprene, poly(alphamethylstyrene), polydiene-polyaromatic arene copolymers, resin esters and mixtures thereof. These could be added in amounts up to 20 percent of the monomer mixture, preferably 0–10 percent.

Also usable are copolymerizable ionic surfactants to improve cohesive strength and moisture resistance. These include polyalkylene polyalkoxy ammonium sulfate (e.g., "MAZON" SAM-211 available from PPG Industries) and alkyl allyl sulfosuccinates (e.g., "TREM" LF40 available from Diamond Shamrock Co.), as well as those described in PCT application No. WO 89/12618, U.S. Pat. No. 3,983,166, incorporated herein by reference. Other noncopolymerizable ionic and nonionic surfactants can be used above or in blends instead of the copolymerizable surfactants but are less preferred. The surfactants can be used in amounts of from 0 to 10 percent of the total monomer mixture, preferably 1.5 to 5 percent.

The pressure-sensitive adhesive matrix of the invention also contains initiator to aid in polymerization of the monomers. Suitable initiators include thermally-activated initiators where the initiator can be water or oil soluble. Suitable oil soluble initiators include azo, and diazo compounds, hydroperoxides, peroxides, and the like. Water soluble initiators include persulfates such as potassium persulfate. Generally, the initiator is present in an amount of from about 0.01 percent to about 3.0 percent preferably 0.1 to 0.5 percent, based on the total monomer component.

Where superior cohesive strengths are desired, the pressure-sensitive adhesive matrix may also be crosslinked. Preferred crosslinking agents for the acrylic pressure-sensitive adhesive matrix are multifunctional acrylates such as 1,6-hexanediol diacrylate as well as those disclosed in U.S. Pat. No. 4,379,201 (Heilmann et al.), incorporated herein by reference. Each of the crosslinking agents is useful in the range of from about 0.01% to about 3%, preferably 0.1 to 1 percent, of the total components.

Other useful materials which can be blended into the adhesive matrix include, but are not limited to, fillers, pigments, plasticizers, tackifiers, fibrous reinforcing agents, foaming agents, antioxidants, stabilizers, fire retardants, and rheological modifiers. Chain transfer agents, such as carbon tetrabromide, mercaptane or alcohols, can be used in the monomer mixture to adjust the molecular weight of the monomer.

The adhesive is formulated by mixing water and the monomers with optional hydrophobic polymer, surfactants, chain transfer agent, crosslinker and then heating under an inert ($O_2$ free) atmosphere while treating with initiator. The reaction latex mixture can be mixed with other optional additives and coated with microspheres, discussed below, as an adhesive mixture by any conventional method.

The substrate 6 can be treated, such as by corona discharge, to improve adhesion by the microsphere/adhesive matrix.

The acrylate pressure-sensitive adhesive matrix can also contain tacky microspheres in an amount ranging from 1 to 40 parts microspheres to 99 to 60 parts adhesive matrix, preferably 1 to 20 parts microspheres. The inherently elastic or tacky, solvent and water insoluble (such that a portion of the polymer is water and solvent insoluble), crosslinked, solvent or water dispersible, polymeric microspheres are formed primarily from free radically polymerizable monomers preferably capable of forming homo- or co-polymers having glass transition temperatures or melt transition temperatures generally less than −10° C. Preferred are vinyl esters, acrylates and methacrylates which will produce homopolymer or copolymers having glass transition temperatures less than 0° C., preferably less than −10° C. Suitable acrylates and methacrylates include isooctyl acrylate, isononyl acrylate, isoamyl acrylate, 2-ethylhexyl acrylate, n-butyl acrylate, and sec-butyl acrylate; other acrylates and methacrylates can be used provided that the overall Tg is less than that specified, such other monomers include terbutyl acrylate, isobornyl acrylate, butyl methacrylate, vinyl acetate, acrylonitrile, isononal acrylate, isodecyl acrylate, isodecyl methacrylate, sec-butyl acrylate, isoamyl acrylate, 2-methylbutyl acrylate, 4-methyl-2-pentyl acrylate, isodecyl acrylate, and ethyl acrylate; mixtures thereof with vinyl esters and other suitable comonomers, such as styrene and substituted styrenes or polar monomers.

Hydrophilizing agents or components can also be used with the monomers and produce microspheres with pendent hydrophilic moieties. The hydrophilizing agents can act as crosslinkers when they are multifunctional. Preferred are free radically reactive hydrophilic oligomers (a polymer having a low number of repeating units, generally 2 to 20) and/or polymers (having more repeating units than an oligomer) including but are not limited to those selected from the group consisting of poly(alkylene oxides), such as poly-(ethylene oxide), poly(vinyl methyl ether), poly(acrylamide), poly(n-vinylpyrrolidone), poly(vinyl alcohol), cellulose derivatives and mixtures thereof.

The microspheres preferably comprise at least 70 parts of at least one free radically polymerizable monomer, optionally up to about 30 parts of one or more polar monomers (generally somewhat oil-soluble and water soluble such as olefinic mono or dicarboxylic acids like acrylic acid), and about 0 to about 30 parts of at least one hydrophilizing component. Additional initiators and/or multifunctional crosslinker and other additives may also be used in addition to the above, as required.

More preferably, the microspheres comprise about 80 to about 100 parts, most preferably 90 to 100 parts, of free radically polymerizable monomer selected from the group consisting of alkyl acrylate esters, alkyl methacrylate esters, vinyl esters, and mixtures thereof where the alkyl group is a $C_4$ to $C_{12}$ alkyl, optionally about 0 to about 10 parts of at least one polar monomer, and optionally about 0 to about 10 parts of a hydrophilizing component. Most preferably the microspheres comprise about 95 to about 99.9 parts of free radically polymerizable monomer, about 0 to about 5.0 parts of a hydrophilizing component, and, optionally, about 0.1 to about 5.0 parts of a polar monomer. The microsphere could be hollow or solid as is known in the art.

The microspheres typically have average diameters of at least about 1 micron, preferably in the range of about 1 to about 300 microns, and most preferable about 1 to 150 microns, or most preferably 20 to 150 microns. When the microspheres are hollow, the voids typically range in size from less than 1 micron up to about 100 microns or larger.

When this acrylate adhesive is used on the fastening tape tab portion generally the adhesive-to-substrate bond is formed by the release tape tab portion adhesive layer. This acrylate adhesive can also be used at least on the free ends of known diaper fastening tape tabs.

In the FIG. 1 embodiment the fastening tape tab portion 5 is shown secured to an inward part of the distal side edge of the diaper chassis 1 providing a region 15 which overlaps with the adhesive-to-substrate bond area 13. Generally the release tape tab portion 4 can be placed anywhere inward of the outer side edge of the diaper chassis 1, such that at least a portion of the fastening tape tab portion 5 extends outward beyond the side edge of the diaper chassis 1.

Figure 2:
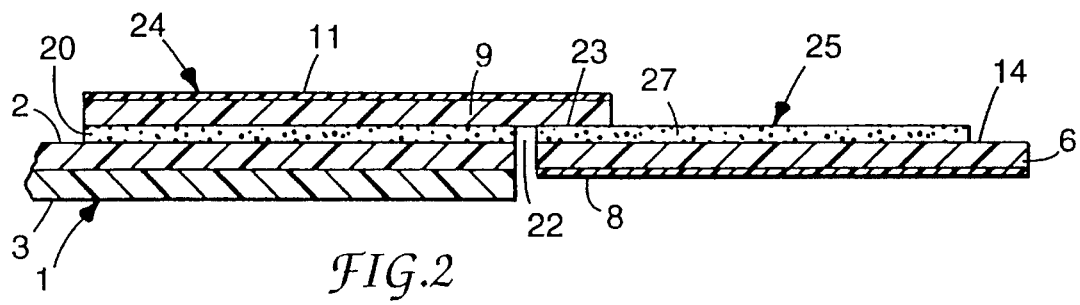
FIG. 2 is a side cross-sectional view of a second embodiment of the invention closure tape laminate on a diaper side edge.

In the FIG. 2 embodiment like numerals indicate identical elements shown in FIG. 1. The adhesive-free substrate region is provided on a distal end portion of the release tape tab portion 24 rather than the fastening tape tab portion 25 as in FIG. 1. The adhesive-to-substrate bond area 23 is between substrate 9 of the release tape tab portion 24 and the fastening tape tab portion adhesive layer 27. Adhesive layer 20 of the release tape tab portion 24 is zone coated to provide an uncoated substrate region for forming the adhesive to-substrate bond 23. The fastening tape tab portion adhesive layer 27 would be zone coated to provide the adhesive-free substrate region.

Figure 3:
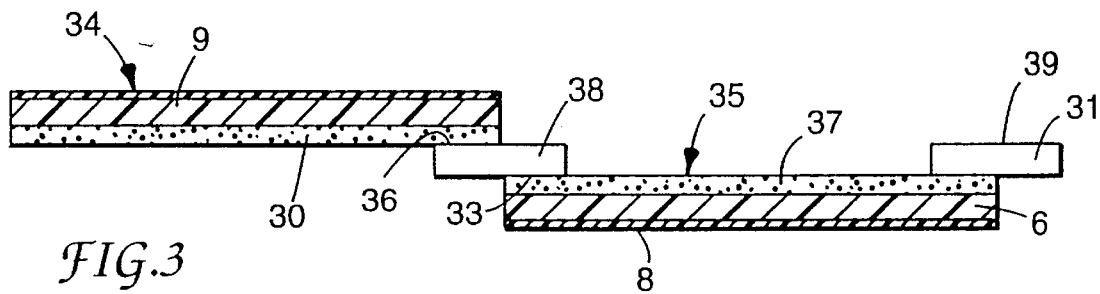
FIG. 3 is a side cross-sectional view of a third embodiment of the invention closure tape laminate.

In the FIG. 3 embodiment the adhesive-to-substrate bond is formed by an intermediate bonding substrate 38, which directly bonds to the release tape tab portion adhesive layer 30 and the fastening tape tab portion adhesive layer 37 creating two adhesive-to-substrate bond portions 33. In this embodiment both the release tape tab portion 34 and the fastening tape tab portion 35 are formed with substrates (6 and 9) fully coated with adhesive layers 30 and 37. The adhesive-free fingerlift region 39 is created by attaching a fingerlift substrate 31 to a distal end portion of the fastening tape tab portion 35. Fingerlift substrate 31 could be used to form a fingerlift in any of the other embodiments of the invention as would be apparent to one of skill in the art.

Figure 4:
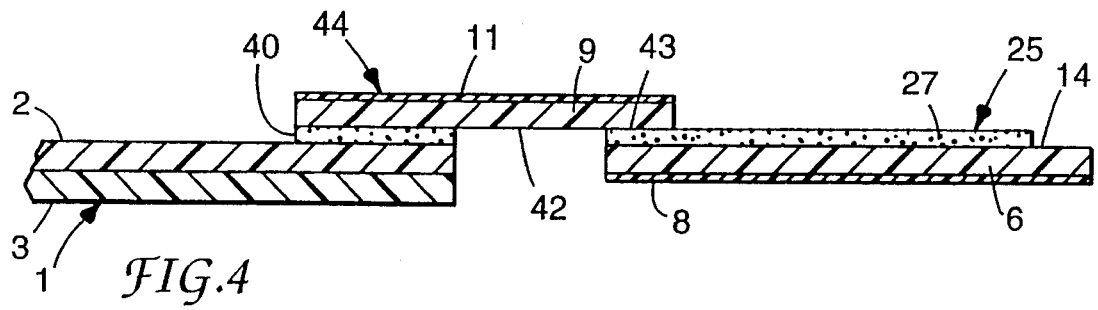
FIG. 4 is a side cross-sectional view of a fourth embodiment of the invention closure tape on a diaper side edge.

FIG. 4 illustrates a fourth embodiment of the invention where the adhesive-free substrate region 42 is enlarged, which would be suitable for release tape tab portions 44 provided with more aggressive adhesive layers 40. In the FIG. 5 variation of the FIG. 4 embodiment, the adhesive-free substrate region 52 is elastic, which can be accomplished by using suitable elastic substrates 59 formed by an elastic film or web or by selecting a film or web which is selectively elastic at least in the adhesive-free substrate region 52 not forming the adhesive-to-substrate bond area 53.

Figure 5:
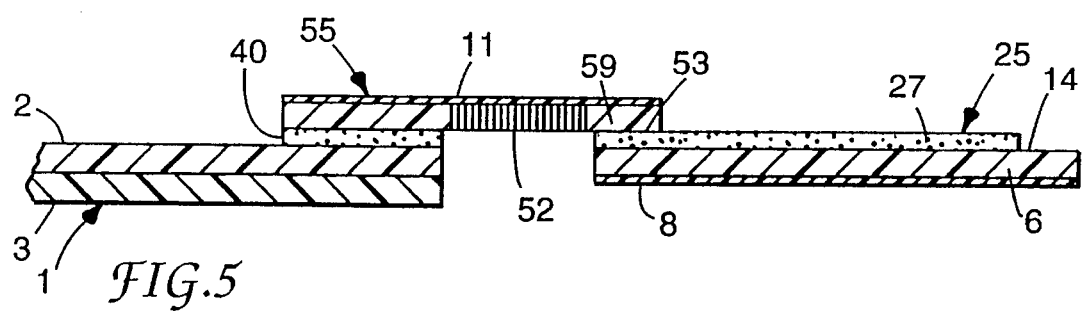
FIG. 5 is a side cross-sectional view of a fifth embodiment of the invention closure tape on a diaper side edge.
Figure 6:
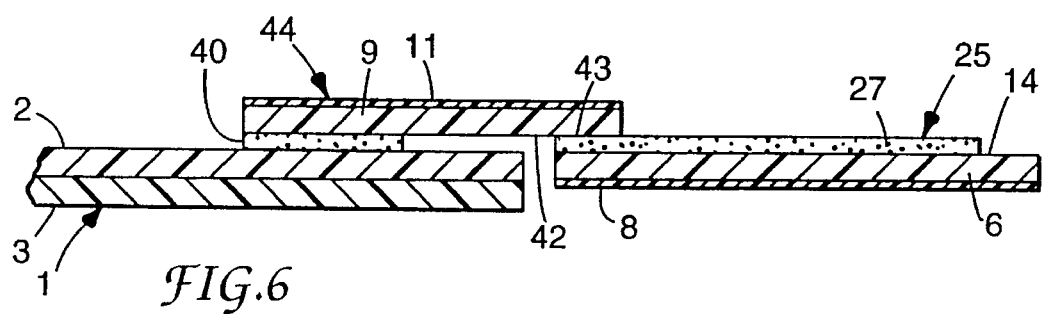
FIG. 6 is an alternative placement of the FIG. 4 embodiment inward of the diaper side edge.

FIG. 6 is a alternative attachment option for the FIG. 4 and 5 embodiments.

Figure 7:
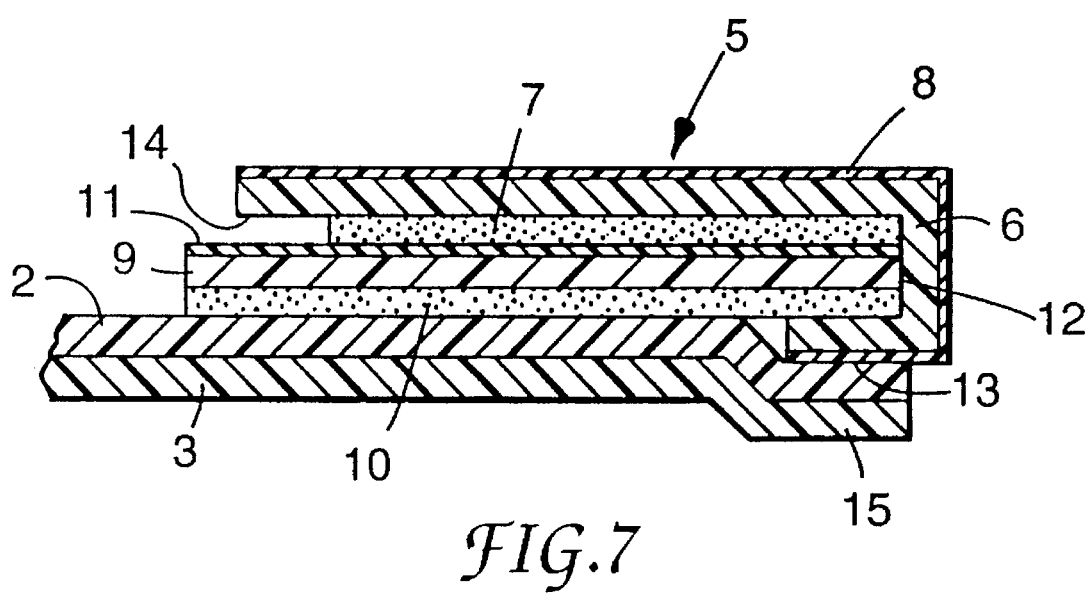
FIG. 7 is a side cross-sectional view of the FIG. 1 embodiment as it would appear prior to use.

FIG. 7 is a depiction of the FIG. 1 embodiment as it would appear in the folded form prior to use.

The invention laminate closure tape can easily be formed by separately laminating a release tape tab portion with a fastening tape tab portion on the diaper line from separate tape components supplied in roll form. However, alternatively the laminate closure tape could be provided in a prelaminate roll form and directly cut into tabs by the diaper manufacturer. The direct adhesive-to-substrate bond provides secure attachment between the two tape tab portions without the risk of cohesive failure generally created by direct adhesive-to-adhesive bonding. The use of separate release and fastening tape tab portions provides opportunities to formulate the release tape tab portion adhesive layer to permanently bond the laminate closure tape at one end while allowing the fastening tape tab portion adhesive layer to be formulated to releasably secure to a diaper backsheet or the like in a reclosable diaper tape closure system. However, the adhesive on the fastening tape tab portion can be rendered more aggressive when the backsheet, or like surface, is suitably reinforced as is known in the art.

With a diaper or the like provided with a outer fibrous web engagable with a male mechanical fastener the fastening tape tab portion can be provided with a male mechanical fastening element on the first face. The male mechanical fastening element can be attached to the fastening tape tab portion with the fastening tape tab portion adhesive layer. The male mechanical fastening element can cover all or just a portion of the fastening tape tab portion adhesive layer. Alternatively the fastening tape tab portion can be formed from a male mechanical fastening element provided with a region on the first face free of mechanical fastening structures, such as hooks or mushrooms shaped structures, for forming the adhesive-to-substrate bond. With these embodiments the release tape tab portion need not have a release surface if no portion of the fastening tape tab adhesive layer is exposed. Further the release tape tab portion can be shortened allowing the male mechanical fastening element mechanical fastening structure to engage with the diaper fibrous topsheet layer 2 when the fastening tape tab portion is folded onto the release tape tab portion.

EXAMPLE AND COMPARATIVE EXAMPLE

Pressure-sensitive adhesive (PSA) tapes were prepared by solvent coating a PSA onto the smoother side of a 3.0 mil (75 microns) thick matte/matte polypropylene film (prepared from #5A95 polypropylene resin available from Shell Chemical Co.). The PSA composition was 49.5 weight % Kraton™ 1119 (a styrene-isoprene-styrene block copolymer available from Shell Chemical Co.), 49.5 weight % Wingtack™ Plus (a solid $C_5$ tackifying resin available from Goodyear Chemical Co.), and 1.0 weight % Irganox™ 1076 (a hindered phenol antioxidant available from Ciba-Geigy). The PSA was coated from a 50% solids solution in a 77:23 toluene:heptane solvent mixture. The final PSA coating thickness was 7 grains/24 in$^2$ (29 microns).

Shear adhesion (PSA-to-film substrate) was measured by determining the length of time it took for a 1 in×0.25 in (2.5 cm×0.63 cm) sample of the adhesive tape to shear off of the smooth side of a 4.0 mil (100 microns) thick cast polypropylene film having a matte finish on one side (prepared from #7C50 resin, a propylene ethylene impact copolymer available from Shell Chemical Co.) under a one kilogram load. A 1 in×2 in (2.5 cm×5.1 cm) area of the PSA tape was placed adhesive side down onto the smooth side of a 2 in×6 in (5.1 cm×15.2 cm) piece of the polypropylene film and was rolled down onto the film using two passes of a 4.5 lb (2 kg) hard rubber roller. The overlap area between the tape and the film was 1 in×0.25 in (2.5 cm×0.63 cm). The film/PSA tape laminate was then hung vertically in a 40° C. oven for 15 minutes after which a one (1) kilogram weight was hung from the PSA tape creating a shear load at a 180 degree angle. The time that it took for the weight to drop was recorded as a measure of the shear adhesion. An average of five tests gave a shear adhesion value of >9900 minutes.

For comparison, PSA-to-PSA shear adhesion was also measured by the procedure described above except that two 1 in (2.5 cm) width pieces of PSA tape were laminated to each other (PSA-to-PSA) so that there was a 1 in×0.25 in (2.5 cm×0.63 cm) overlap area between the two tapes. An average of five tests gave a PSA-to-PSA shear adhesion value of 236 minutes, which is considerably lower than the PSA-to-film substrate shear adhesion value.

We claim:

1. A pressure-sensitive adhesive tape closure system comprising a closure tape laminate comprised of a fastening tape tab portion having a first substrate with a first and second face and a release tape tab portion having a second substrate with a first face and a second face, the release tape tab portion second substrate first face having a first adhesive layer with no adhesive layer on said second face, said fastening tape tab portion first substrate first face having a fastening surface with no adhesive on said second face, with an end of said fastening tape tab portion first substrate connected to an end of said release tape tab portion second substrate by at least one adhesive layer-to-substrate bond, wherein at least a portion of the release tape tab portion first face, and the fastening tape tab portion first face or an intermediate substrate is not coated with an adhesive layer such that the fastening tape tab portion fastening surface and the release tape tab portion adhesive layer do not form an adhesive-to-adhesive bond and said fastening tape tab portion first face is in face-to-face contact with said release tape tab portion second face when the laminate is folded at said adhesive layer-to-substrate bond region.

2. The tape closure system of claim 1 wherein said fastening tape tab portion fastening surface comprises a mechanical fastening element.

3. The tape closure system of claim 1 wherein said fastening tape tab portion first substrate fastening surface comprises a second adhesive layer and said release tape tab portion second face has a release surface.

4. The tape closure system of claim 3 wherein said at least one adhesive layer-to-substrate bond is a direct bond between the fastening tape tab portion first substrate second adhesive layer and an end portion of the first face of said release tape tab portion second substrate not coated with said first adhesive layer.

5. The tape closure system of claim 3 wherein said at least one adhesive layer-to-substrate bond is a direct bond between the release tape tab portion second substrate first adhesive layer and an end portion of the first face of said fastening tape tab portion first substrate not coated with said second adhesive layer.

6. The tape closure system of claim 3 wherein said at least one adhesive layer-to-substrate bond are two adhesive layer-to-substrate bonds the first adhesive layer-to-substrate bond being between the fastening tape tab portion first substrate adhesive layer and an third intermediate substrate first face and the second adhesive layer-to-substrate bond being between the release tape tab portion second substrate adhesive layer and said third intermediate substrate second face.

7. The tape closure system of claim 3 wherein said release tape tab portion second substrate second face release surface is formed by a release coating.

8. The tape closure system of claim 3 wherein said fastening tape tab portion second substrate second face is provided with a release surface.

9. The tape closure system of claim 4 wherein said release tape tab portion second substrate is provided with an adhesive-free region between said release tape tab portion second substrate having said adhesive layer and the adhesive layer-to-substrate bond.

10. The tape closure system of claim 9 wherein at least said adhesive-free region of said second substrate is elastic.

11. The tape closure system of claim 5 wherein at least said fastening tape tab portion first substrate is provided with an adhesive-free region between said fastening tape tab portion first substrate adhesive layer and said adhesive layer-to-substrate bond.

12. The tape closure system of claim 3 wherein said fastening tape tab portion first substrate adhesive layer is less aggressive than said release tape tab portion second substrate adhesive layer.

* * * * *